United States Patent [19]

Jensen et al.

[11] Patent Number: 4,578,390
[45] Date of Patent: Mar. 25, 1986

[54] HYDROXYBENZYLAMINO DERIVATIVES AS ANTI-INFLAMMATORY AGENTS

[75] Inventors: Norman P. Jensen, New Providence; Michael N. Chang, Westfield, both of N.J.

[73] Assignee: Merck & Co., Inc., Rahway, N.J.

[21] Appl. No.: 484,406

[22] Filed: Apr. 13, 1983

Related U.S. Application Data

[63] Continuation-in-part of Ser. No. 330,542, Dec. 14, 1981.

[51] Int. Cl.$^4$ .................. C07D 333/36; C07D 285/10; A61K 31/38; A61K 31/41
[52] U.S. Cl. .................. 514/255; 514/447; 514/443; 514/472; 514/465; 514/426; 514/415; 514/370; 514/367; 514/362; 514/398; 514/313; 514/310; 514/352; 514/381; 514/383; 548/135; 548/329; 548/557; 548/558; 549/57; 549/68
[58] Field of Search ................ 548/135, 329, 557, 558; 549/68, 57; 514/447, 443, 472, 465, 426, 415, 370, 367, 362, 398, 313, 310, 352, 255, 381, 383

[56] References Cited

U.S. PATENT DOCUMENTS 2,784,138 3/1957 Wegler ............................. 424/304
3,505,330 7/1970 Davoll .............................. 544/291
3,996,278 12/1976 Schlager .......................... 260/559
4,152,452 5/1979 Douglas ........................... 424/304

FOREIGN PATENT DOCUMENTS 117047 5/1975 Japan ................................ 514/255
190466 11/1976 Netherlands ..................... 514/255

OTHER PUBLICATIONS

Jakohiec, Arch. Immunol. Ther. Exp. 27, 795 (1979).
Gieldanowski, Arch. Immunol. Ther. Exp. 26, 921 (1978).
Shvedov et al. Khim-Farm Zh. 13, 34 (1979).
Renault et al., C. R. Hebd. Seances Acad. Sci. Ser. C 280 1041 (1975).
Chemical Abstracts, vol. 86, No. 9, p. 366, No. 54830q (Feb. 1977).
Archiv der Pharmazie, vol. 298, No. 7, pp. 423–434 at p. 429 (1965).

Primary Examiner—Robert Gerstl
Attorney, Agent, or Firm—Theresa Y. Cheng; Mario A. Monaco

[57] ABSTRACT

Hydroxybenzylamino derivatives have been prepared from an appropriate hydroxybenzaldehyde and an amine followed by reduction. These compounds are found to be active topical anti-inflammatory agents.

10 Claims, No Drawings

HYDROXYBENZYLAMINO DERIVATIVES AS ANTI-INFLAMMATORY AGENTS

BACKGROUND OF THE INVENTION

The present application is a continuation-in-part of copending application Ser. No. 330,542 filed Dec. 14, 1981.

The present invention relates to novel hydroxybenzylamino derivatives useful as topical anti-inflammatory agents. We have found that the novel compounds are active in vitro in both the peritoneal macrophage assay and the polymorphonuclear leukocyte assay. We have also found that these compounds are active in vivo in the topical mouse ear assay and the U.V. erythema assay for anti-inflammatory agents. However, these compounds tend to be inactivated in vivo and thereby are devoid of any significant systemic effects.

Recent studies demonstrated that macrophages participate in the development and progression of chronic inflammatory diseases such as rheumatoid arthritis. During the progression of inflammatory conditions, there is generally an appearance and/or presence of macrophages and lymphocytes, especially macrophages and polymorphonuclear leukocytes. Macrophages are known to secrete various products in response to inflammatory stimuli. For example:

(1) Neutral proteinases—the destructive peptide bond cleaving enzyme which has been shown to be directly involved in rheumatoid cartilage destruction; and (2) Prostaglandins (PG) (e.g., $E_2$ and $I_2$ by mouse peritoneal macrophages) and other arachidonic acid derivatives derived from both the cyclooxygenase and the lipoxygenase pathways.

These arachidonic acid oxygenation products have been identified as the critical mediators of various acute inflammatory conditions.

Accordingly, pharmacological agents which are capable of inhibiting the formation of, the release of a mediator from, or the function of macrophages of polymorphonuclear leukocytes may also be effective agents in the treatment of rheumatoid arthritis, emphysema, bronchial inflammation, osteoarthritis, acute respiratory distress syndrome, spondylitis, lupus, gout, psoriasis and other inflammatory diseases.

Regarding the topical mouse ear assay, it has been previously established that classical nonsteroidal anti-inflammatory agents such as indomethacin and steroidal anti-inflammatory agents such as dexamethasone are active in this assay.

With respect to the U.V. erythema assay, it has been shown previously that the U.V. erythema condition is partially the result of a local release of prostaglandins derived oxidatively from arachiodonic acid by the action of PG synthetases, e.g., cyclooxygenase. Therefore, pharmacological agents which inhibit the erythema are generally considered to be active topical anti-inflammatory agents.

Furthermore, anti-inflammatory agents which are not significantly systemically active are advantageous in the sense that they are not subject to the adverse efects, e.g., gastrointestinal ulcerations and bleeding that often plagued users of systemic NSAIAs (non-steroidal anti-inflammatory agents). Accordingly, an object of this invention is to provide novel hydroxybenzylamino derivatives as topical anti-inflammatory agents useful in the treatment of dermal inflammatory conditions and prusitus such as sunburn, erythema, eczema, contact dermatitis, and allergic dermatitis, and psoriasis and for topical application to prevent periodontal disease.

Another object of this invention is to provide appropriate processes for the preparation of the subject novel compounds.

Still a further object of the present invention is to provide a pharmaceutically acceptable composition containing an effective amount of the active compound for the treatment of various dermatological inflammatory conditions.

Finally, it is the ultimate object of this invention to develop a method of treating dermal inflammation via the administration of an effective amount of the novel compounds as well as a pharmaceutically acceptable composition thereof to a mammalian species in need of such treatment.

DETAILED DESCRIPTION OF THE INVENTION

This invention relates to novel derivatives of hydroxybenzylamine of the structural formula (I):

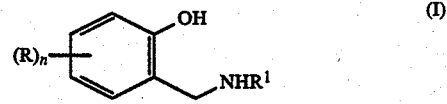

or a pharmaceutically acceptable salt thereof,
wherein R is
- (a) hydrogen;
- (b) halo especially fluoro, chloro or bromo;
- (c) loweralkoxy especially $C_{1-6}$ alkoxy, e.g., methoxy, ethoxy, isopropoxy, t-butoxy or cyclohexyloxy, or —OCH$_2$O—;
- (d) lower alkylthio especially $C_{1-6}$ alkylthio, or $C_{1-6}$ haloalkylthio e.g., methylthio, ethylthio, trifluoromethylthio or cyclohexylthio;
- (e) lower alkyl sulfinyl especially $C_{1-6}$ alkyl sulfinyl, e.g., methyl sulfinyl, i-propyl sulfinyl, and cyclopentyl sulfinyl;
- (f) lower alkyl sulfonyl especially $C_{1-6}$ alkyl sulfonyl such as methyl sulfonyl, ethyl sulfonyl and n-butyl sulfonyl;
- (g) unsubstituted or substituted phenyl loweralkoxy such as benzyloxy;
- (h) loweralkyl especially $C_{1-6}$ alkyl such as methyl, ethyl, propyl, t-butyl, pentyl, benzyl, cyclopropyl, cyclopentyl or cyclohexyl;
- (i) loweralkenyl especially $C_{2-6}$ alkenyl, for example, vinyl, allyl, and buten-2-yl;
- (j) lower alkanoyl especially $C_{1-6}$ alkanoyl such as formyl, acetyl or i-propanoyl;
- (k) haloloweralkyl especially $C_{1-6}$ haloalkyl such as trifluoromethyl;
- (l) —COOH;
- (m) aryl especially phenyl or substituted phenyl, e.g., 4-methoxyphenyl, 2,4-difluorophenyl or 3-chlorophenyl; or
- (n) aryloxy especially phenoxy;
- (o) cyano;
- (p) hydroxyloweralkyl especially hydroxy $C_{1-3}$ alkyl such as —CH$_2$OH;
- (q) heteroaryl as defined below; or
- (r) loweralkanoyloxy especially acetyloxy;

$R^1$ is (a) phenyl substituted with $R^2$ wherein $R^2$ can be R or H, especially 2-hydroxymethyl, 2-acetyloxymethyl, 2,3-methylenedioxy, 4-aryloxy, 4-heteroaryl or 5-hydroxycarbonyl;
(b) unsubstituted or substituted heteroaryl, for example:
(1) thienyl;
(2) benzothienyl;
(3) furyl;
(4) benzofuryl;
(5) pyrryl;
(6) indolyl;
(7) thiazolyl;
(8) benzoythiazolyl;
(9) thiadiazolyl;
(10) benzothiadiazolyl;
(11) imidiazolyl;
(12) benzimidazolyl;
(13) quinolyl;
(14) isoquinolyl;
(15) pyridyl;
(16) pyrazinyl;
(17) tetrazolyl; or
(18) triazolyl The heteroaryl above can be substituted with one or more of R, e.g., $C_{1-6}$ alkyl, $C_{1-6}$ alkanoyl, $C_{1-6}$ haloalkyl, halo, cyano, or hydroxy $C_{1-3}$ alkyl.

However, when $R^1$ is phenyl or phenyl substituted with $R^2$ which is other than
(a) hydroxyloweralkyl such as hydroxymethyl;
(b) $C_{1-6}$ alkanoyloxy such as acetyloxymethyl;
(c) methylenedioxy;
(d) aryloxy;
(e) heteroaryl; or
(f) hydroxycarboxyl,
R can only be
(a) trifluoromethylthio;
(b) hydroxyloweralkyl especially hydroxymethyl;
(c) $C_{1-6}$ alkanoyloxy loweralkyl especially acetyloxymethyl; or
(d) heteroaryl; and
n is 1 to 4.

In a preferred embodiment of this invention,
R is
(a) hydrogen;
(b) loweralkoxy;
(c) lower haloalkylthio or loweralkylthio;
(d) halo; or
(e) loweralkanoyl;
(f) lowerhaloalkyl especially trifluoromethyl;
(g) hydroxyloweralkyl; or
(h) cyano;
$R^1$ is unsubstituted or substituted heteroaryl; and
n is 1 to 3.

In a more preferred embodiment of this invention,
R is
(a) hydrogen;
(b) $C_{1-3}$ alkoxy such as methoxy, ethoxy or isopropoxy;
(c) $C_{1-3}$ haloalkylthio such as trifluoro methylthio;
(d) $C_{1-3}$ alkanoyl such as acetyl; or
(e) fluoro or chloro;
$R^1$ is unsubstituted or substituted heteroaryl; and
n is 1 or 2.

Representative compounds of the present invention includes:

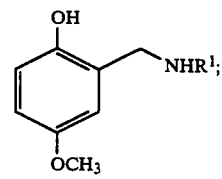
(a)

wherein $R^1$ is:

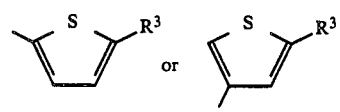
(1)

where $R^3$ represents H, $CH_3$, F, Cl, $—COCH_3$, $—CN$ or $—COOR^4$ where $R^4$ represents loweralkyl;

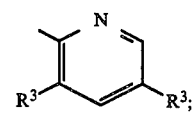
(2)

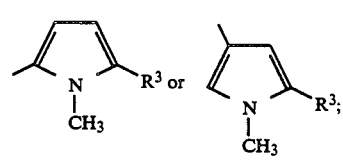
(3)

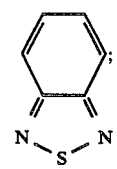
(4)

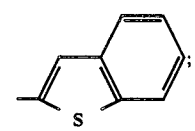
(5)

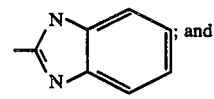
(6)
; and

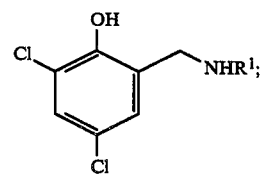
(b)

wherein $R^1$ is:

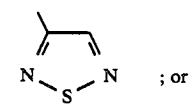
(1)
; or

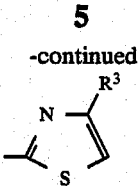

The novel compounds of the present invention are prepared from a process comprising:

Step (1):
treating an appropriately substituted 2-hydroxy-benzaldehyde of the structural formula (II)

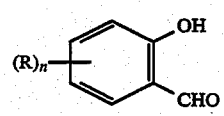

with an amine of formula $R^1NH_2$ to form a Schiff-base; and

Step (2):
treating the resulting Schiff-base with a reducing agent such as hydrogen in the presence of a catalyst, e.g., Pd/C or sodium tetrahydroboron.

In Step (1), the Schiff-base formation is well-documented. See M. M. Sprung, Chem. Rev., 26, 297 (1940); R. W. Layer, Chem. Rev., 63, 489 (1963); and G. Hilgetag and A. Martini, Preparative Organic Chemistry, Wiley-Interscience, pp. 504–508 (1968). Generally, the benzaldehyde is treated with neat amine or a solution thereof at relatively low temperatures, e.g., from about 0° C. to about 25° C. with adequate stirring until the reaction is substantially complete. The solution of the amine is usually prepared by dissolving the amine in an organic solvent preferably water, lower alcohol such as methanol, ethanol, isopropyl alcohol or an aqueous solution thereof. Under optimum conditions the reaction usually takes from about 1 to about 24 hours.

In most cases, Step (2) can be conveniently merged into Step (1) by the simple addition of a reducing agent to the reaction mixture of step (1). The crude Schiff-base in the reaction mixture is thus reduced in situ to the desired hydroxybenzylamino derivatives of formula (I).

The most commonly used reducing agents, among others, are hydrogen in the presence of Pd/C and sodium borohydride. Other metal hydrides, for example, lithium borohydride, lithium aluminumhydride NaCNBH$_3$ and other substituted aluminum or borohydrides may also be used. See H. O. House, Modern Synthetic Reactions, 2nd ed., W. A. Benjamin, Inc., 1972, pp. 45–54.

The reduction is usually conducted at relatively low temperatures, e.g., from about 0° to about 30° C., preferably below 25° C. A solvent is usually required. The commonly used solvents for each reducing agent are summarized below in Table I.

TABLE I

| Reducing Agent | Useful reaction solvents |
|---|---|
| NaBH$_4$ | H$_2$O, CH$_3$OH, EtOH, i-PrOH, diglyme |
| LiBH$_4$ | Tetrahydrofuran, diglyme |
| LiAlH$_4$ | Diethylether, tetrahydrofuran, 1,2-dimethoxyethane, and diglyme |
| H$_2$/Pd/C | Ethylacetate, ethanol, water, acetic acid |

Usually the reduction is substantially complete within from about 1 hour to about 48 hours. However, under optimum conditions, the reaction may take only 1 to 6 hours.

The starting materials in the preparation of the novel hydroxybenzylamine derivatives are mostly commercially available or can be easily prepared via conventional methods, for example, 4-(3,3-dimethylbutyrylamino)aniline is simply derived from the reaction between 4-nitro-aniline and 3,3-dimethylbutyryl chloride followed by hydrogenation.

As the novel compounds of this invention are organic bases, their pharmaceutically acceptable salts are those resulting from the neutralization of the base with an acid. The acid employed is usually an inorganic acid such as a hydrohalic acid such as hydrochloric or hydrobromic acid; sulfuric acid; nitric acid; or phosphoric acid. An organic acid such as maleic, fumaric, tartaric, citric, acetic, salicyclic, succinic, benzoic, benzenesulfonic, naphthalene disulfonic, glutamic, lactic or isethionic acid is also commonly used. Generally the neutralization is conducted in an inert solvent such as water; a C$_{1-3}$ alkanol such as methanol, ethanol or isopropanol; a C$_{3-6}$-ketone such as acetone, or ethylmethyl ketone; an ethereal solvent such as diethyl ether, tetrahydrofuran or dioxane; acetonitrile; or an aromatic solvent such as toluene. Mixtures of the above described solvents are also employed. Generally the neutralization is carried out in aqueous ethanol, at 0°–75° C., preferably at 0°–25° C., followed by filtration to collect the salts.

This invention also relates to a method of treating topical inflammation in patients in need of such treatment. Generally, a sufficient amount of a compound of formula (I) or a pharmaceutical composition thereof, particularly an especially preferred compound, is administered to the patient as the active constituent.

The topical mouse ear assay (TME) is the preferred method by which the novel compounds of the present invention are evaluated for its effect on inflammatory responses elicited by topically applied phorbol myristate acetate (PMA) or topically applied arachidonic acid (AA). The inflammatory responses may be in the form of edema (measured by wet weight); vascular permeability (measured by $^{125}$I-BSA accumulation); or PMN infiltration (measured by myloperoxidase activity). A protocol of the assay and some results derived therefrom are summarized in Table II.

TABLE II Topical Mouse Ear Assay

Method: The right ears of mice (5 mice per group) were treated topically with either 5 μl PMA or 1000 μg AA alone or with the test compound in 25 μl of vehicle. The vehicle was water/pyridine/acetone (1:2:97). A control group of mice received the vehicle only. The mice were allowed food and water ad libitum during the treatment period; 2 hours for AA and 4 hours for PMA. The mice were sacrificed by cervical dislocation and a 6 mm diameter disc of tissue punched from both the treated and untreated ears. The tissue biopsies were immediately weighed and the weight increase of the treated ear relative to the weight of the untreated ear determined.

For the determination of vascular permeability, 1 μCi $^{125}$I-bovine serum albumin ($^{125}$I-BSA) was administered in 0.5 ml phosphate buffered saline 15 min prior to the topical application. At the termination of the experiment, the amount of radioactivity in both the treated and untreated ear biopsies was determined and the increased amount of radioactivity in the treated tissue relative to the amount of radioactive in the untreated tissue determined.

As a measure of PMN infiltration, the amount of myleoperoxidase (MPO) activity in the same tissues was determined. The tissue biopsies were homogenized into 1 ml 0.5% hexadecyltrimethylammonium bromide and centrifuged for 45 min. at 1200×g. Aliquots 40 μl, of the supernatant phases were assayed for MPO activity by a colorimetric method devised by H. Dougherty for automated Titertek analysis. The MPO activity is expressed as the $OD_{450}$ of the treated ear homogenate minus the $OD_{450}$ of the non-treated ear homogenate.

All of the data are expressed as the mean±SEM, N=5 mice/group.

Results: The effect of 2-(2-hydroxy-5-methoxybenzylamino)thiophene (A); 4-(2-hydroxy-5-methoxybenzylamino)-2,1,3-benzothiadiazole (B); and 2-(2-hydroxy-5-methoxybenzylamino)benzimidazole (C)

| Compound | Dosage (μg) | Edema (% inhibition) |
|---|---|---|
| A | 300 | 77 |
| B | 300 | 44 |
| C | 300 | 80 |
| Indomethacin | 1000 | 88 |
| Dexamethasone | 150 | 100 |

The U.V. erythema assay by which topical anti-inflammatory activity is determined, is based on the ability of the compounds of Formula I to inhibit the erythema induced on the skin of guinea pigs by UV radiation. It has been substantiated by recent studies that prostaglandin synthesis and the release thereof may be the primary process involved in the production of erythema. A protocol of the assay and some results thereof are summarized below in Table III.

TABLE III
U.V. Erythema Assay

Procedure

Guinea pigs were depilated and stabilized for 30 minutes. Following anesthesia with Nembutal (35 mg/kg), they were exposed to a U.V. lamp for 45 minutes at a distance of seven inches from the abdominal surface. Compound was applied topically (seven applications in a total of 0.1 ml vehicle) 15 minutes post exposure. The surface was then gently washed and read two hours post treatment.

Vehicle 1774—85% EtOH, 12% Propylene Glycol, 3% Methyl Salicylate

| | Erythema Scoring | |
|---|---|---|
| Designation | Numerical Score | Description |
| Negative | 0 | No erythema (normal skin color) |
| Trace | +1 | Faint pink in some areas |
| Slight | +2 | Faint pink over entire site |
| Slight-Moderate | +3 | Faint pink to red |
| Moderate | +4 | Red |
| Marked | +5 | Red to purplish red |

Evaluation of Erythema

A numerical value 0–5 was assigned to the degree of erythema observed under standard lighting conditions. Drug effect on the developing erythema was calculated as follows:

$$\% \text{ suppression} = \frac{\left(\begin{array}{c}\text{score of vehicle}\\\text{treated}\end{array}\right) - \left(\begin{array}{c}\text{Score of drug}\\\text{Treated}\end{array}\right)}{\text{score of vehicle treated}} \times 100$$

Results: % Inhibition of Erythema by (a) N-(2-hydroxy-5-methoxybenzyl)aniline

| Dosage (mg) | % Inhibition (mean of 3 animals) | | | | |
|---|---|---|---|---|---|
| | 2 Hr. | 3 Hr. | 4 Hr. | 6 Hr. | 24 Hr. |
| 0.1 | 19.3 | 16.7 | 15.0 | 6.7 | 0 |
| 0.3 | 55.3 | 50.0 | 46.7 | 35.0 | 0 |
| 1.0 | 80.3 | 91.7 | 76.7 | 63.3 | 26.7 |
| 3.0 | 100 | 100 | 63.3 | 43.3 | 33.3 |

For treatment of inflammation, fever or pain, the compounds of the invention are administered topically, by inhalation spray or rectally in dosage unit formulations containing conventional non-toxic pharmaceutically acceptable carriers, adjuvants and vehicles.

The pharmaceutical compositions containing the active ingredient may be in a form suitable for topical use, for example, aqueous or oily solutions or suspensions, dispersible powders or granules, tinctures, topical aerosol emulsions, creams, ointments, jellies, suppositories or the like. Compositions intended for topical use may be prepared according to any method known to the art for the manufacture of pharmaceutical compositions and such compositions may contain one or more active compounds.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soy bean, lecithin, and esters or partial esters derived from fatty acids and hexitol anhydrides, for example, sorbitan mono-oleate, and condensation products of the said partial esters with ethylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl carproate and ethyl laurate. Suitable glycols include propylene glycol, butylene glycol, polyethylene glycol and the like. Generally, a carboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.2 mg to 140 mg per kilogram of body weight per day are useful in the treatment of the above-indicated conditions (10 mg to 7 gms per patient per day). For example, inflammation is effectively treated by the administration from about 0.5 to 50 mg of the compound per kilogram of body weight per day (25 mg to 5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. Dosage unit forms will generally contain between from about 25 mg to about 1 g of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1

4-(2-hydroxy-5-methoxybenzylamino)-3,3-dimethylbutyrylaminobenzene

Step A: Preparation of (3,3-dimethylbutyrylamino)aniline

Five grams of 4-nitroaniline was stirred in 25 ml of pyridine and 4.95 g of 3,3-dimethylbutyryl chloride was added. The mixture was stirred 15 hours and poured into ice-water. The resultant solid was collected on a filter and dissolved in 200 ml of ethyl acetate and the solution was treated with activated charcoal and concentrated to yield 6.3 g of 4-nitro-3,3-dimethylbutyrylaminobenzene, m.p. 192°–194°. This material was reduced in 200 ml of methanol, at 3 atmospheres of hydrogen in the presence of 5% Pd/carbon. After removal of the catalyst by filtration, concentration of the filtrate gives 5.3 g of product (3,3-dimethylbutyrylamino)aniline, m.p. 138°–140° C.

Step B: Preparation of 4-(2-hydroxy-5-methoxybenzylamino)-3,3-dimethylbutyrylamino benzene A mixture of 2.5 g of 3,3-dimethylbutyrylaminoaniline and 1.84 g of 2-hydroxy-5-methoxybenzaldehyde was stirred in 50 ml of methanol, under a nitrogen atmosphere, for 15 hours. The mixture was then refluxed until tlc indicates that most of the starting material had reacted. After cooling, 0.50 g of NaBH$_4$ was added in two batches, and the mixture was stirred 2.5 hours. After concentration 6.9 g of solid was collected which was triturated with 100 ml of water and enough 2.5N HCl to neutralize the supernatant. 3.95 g of crude product was collected and purified by treatment with activated charcoal and recrystallization from ethyl acetate to give 2.5 g of 4-(2-hydroxy-5-methoxybenzylamino)-3,3-dimethylbutyrylamino benzene, m.p. 126°–129° C.

Following substantially the same procedure as described above but substituting for the starting materials used therein 5-(t-butyl)-2-hydroxy-3-iodobenzaldehyde and 4-acetaminoaniline, there was prepared 4-(5-t-butyl-2-hydroxy-3-iodobenzylamino)acetanilide. M.p. 134.5°–136° C.

EXAMPLE 2

3-(3,5-Dichloro-2-Hydroxybenzylamino)[1,2,5]-thiadiazole

A mixture of 6.9 g of 3,5-dichloro-2-hydroxybenzaldehyde and 3-amino[1,2,5]thiazole hydrochloride was heated at 80° for 18 hours. After cooling, 6.9 g of precipitate, m.p. 174°–175° was collected. This precipitate was added to 100 ml of methanol and the mixture was cooled in an ice-bath before 1.4 g of NaBH$_4$ is added. The mixture was stirred ½ hour and concentrated to give 9.0 g of solid which was purified by trituration with water and enough 2.5N HCl to give a neutral supernatant. The insolubles were then collected, heated with charcoal and recrystallized from methylene chloride to give 5.1 g of 3-(3,5-dichloro-2-hydroxybenzylamino)[1,2,5]thiadiazole. M.p. 131°–132° C.

EXAMPLE 3

N-(2-Hydroxy-5-Methoxybenzyl)Aniline

A mixture of 15.2 g 2-hydroxy-5-methoxy benzaldehyde, 93 g of aniline and 100 ml of methanol was stirred at 25° for 20 hours. The mixture was then cooled with an ice-bath and stirred, and 3.9 g of sodium borohydride was added slowly. The mixture was stirred for 1 hour at 25°, 150 ml of water was added and the pH was adjusted to 7.0 with 2.5N hydrochloric acid. The resultant solid was collected, washed with water and purified by chromatography on silica gel using 3:17 ethyl acetate:n-hexane as an eluant. A 17.7 g yield of N-(2-hydroxy-5-methoxybenzyl)aniline was obtained. M.p. 82°–84°.

EXAMPLE 4

N-(2-Hydroxy-5-methoxybenzyl)Aniline

A mixture of 15.2 g of 2-hydroxy-5-methoxybenzaldehyde, 15 g of aniline and 200 ml of methanol was stirred for 3 hours. The mixture was then hydrogenated at 40 psi in the presence of 2.0 g of 10% Pd/C until 0.1 mole of hydrogen was consumed. The catalyst was removed by filtration and the filtrate was concentrated in vacuo to a yellow oil which was crystallized from ether-n-hexane to yield 18 g of N-(2-hydroxy-5-methoxybenzyl)aniline. M.p. 82.5°–8° C.

Following substantially the same procedure as described above, but substituting for aniline used therein the following compounds:
(1) 2,6-dichloroaniline
(2) 3,5-dimethylaniline
(3) 3,5-dimethoxyaniline
(4) 4-trifluoromethylaniline There are obtained the following corresponding hydroxybenzylaminobenzene derivatives:
(1) 2,6-dichloro-N-(2-hydroxy-5-methoxybenzyl)aniline, m.p.
(2) 3,5-dimethyl-N-(2-hydroxy-5-methoxybenzyl)aniline
(3) 3,5-dimethoxy-N-(2-hydroxy-5-methoxybenzyl)aniline
(4) 4-trifluoromethyl-N-(2-hydroxy-5-methoxybenzyl)aniline

EXAMPLE 5

Following substantially the same procedure as described in Example 3, but substituting for aniline used therein the following heterocyclic amines:
(1) 3-aminoquinoline
(2) 2-amino-4,6-dimethylpyridine
(3) 2-aminobenzimidazole
(4) 4-amino-2,1,3-benzothiadiazole There were obtained the corresponding hydroxybenzyl amine derivatives as listed below:
(1) 3-(2-hydroxy-5-methoxybenzylamino)quinoline, m.p. 95°–96° C.
(2) 2-(2-hydroxy-5-methoxybenzylamino)-4,6-dimethylpyridine, m.p. 101°–103° C.
(3) 2-(2-hydroxy-5-methoxybenzylamino)benzimidazole, m.p. 137°–138° C.
(4) 4-(2-hydroxy-5-methoxybenzylamino)-2,1,3-benzothiadiazole, m.p. 120.5°–122° C.

EXAMPLE 6

2-(2-Hydroxy-5-methoxybenzylamino)-thiophene naphthalene-1,5-disulfonic acid salt

Step A: Preparation of 2-(2-hydroxy-5-methoxybenzylidenimino)thiophene

2-Nitrothiophene (13.0 g, 0.1 mole) was dissolved in 100 ml of ethyl acetate and was hydrogenated at room temperature and 50 psi of hydrogen pressure in the presence of 14.0 g of 10% Pd/C. After three hours no more hydrogen was consumed. The reaction mixture was filtered through celite and the filtrate added directly to 15.2 g (0.1 mole) of 2-hydroxy-5-methoxy-benzaldehyde. The resulting mixture was purified by column chromatography on silica gel using 4:1 n-hexane:ethylacetate as an eluant followed by crystallization from the eluant to give 14.1 g of 2-(2-hydroxy-5-methoxybenzylidenimino)thiophene as a bright yellow crystalline product, m.p. 84°–87° C.

Step B: Preparation of 2-(2-hydroxy-5-methoxybenzylamino)thiophene 2-(2-Hydroxy-5-methoxybenzylidenimino)thiophene (2.33 g) was dissolved in 25 ml of absolute ethanol and stirred under a nitrogen atmosphere at 0° C. One equivalence of sodium borohydride (0.4 g, 10 mmole) was added and the resulting mixture was stirred at 0°–10° C. until the bright yellow color disappeared. Fifteen mililiters of ice water was added and the mixture was extracted with 3×25 ml of ethyl acetate. The combined ethyl acetate extracts were dried with anhydrous sodium sulfate and concentrated to a light yellow oil. Crystallization from ethyl acetate/hexane gave 25 mg (1% yield) of 2-(2-hydroxy-5-methoxybenzylamino)thiophene as a light yellow solid m.p. 109°–110° C.

Step C: Preparation of 2-(2-hydroxy-5-methoxybenzylamino)thiophene naphthalene-1,5-disulfonic acid salt 2-(2-Hydroxy-5-methoxybenzylamino)thiophene (2.3 g) was dissolved in 25 ml of methylene chloride under nitrogen atmosphere and 1.44 g (5 mmole) of solid naphthalene 1,5-disulfonic acid was added. The solid acid dissolved quickly and a white precipitate appeared after 5 minutes of vigorous stirring. After the reaction mixture was stirred ½ hour the resultant precipitate was collected, washed 2×10 ml with methylene chloride and air-dried to give 3.6 g of 2-(2-hydroxy-5-methoxybenzylamino)thiophene naphthalene-1,5-disulfonic acid salt (m.p. 185 dec).

EXAMPLE 7

2-(2-hydroxy-5-methoxybenzylamino)-5-cyano-thiophene and 4-(2-hydroxy-5-methoxybenzylamino)-2-cyano-thiophene

Step A: Preparation of 2-cyano-5-nitro-thiophene/2-cyano-4-nitro-thiophene

To a solution of 10 ml conc. sulfuric acid stirred at 0° C. was added 2-cyano-thiophene (4.0 g, 0.036 mole). Six mililiters of a mixture of 1:1 conc. sulfuric acid and fuming nitric acid was added dropwise to the solution and the temperature was maintained between 10° C. and 15° C. The reaction mixture was allowed to warm-up to room temperature after addition was completed and was stirred for an additional hour. The dark red solution was quenched with 50 ml of ice water and stirred vigorously. A yellow solid precipitated out. The solid was collected on a filter and washed with ice water (2×5 ml). This solid weighed 3.7 g (66%) and is a mixture of 4- & 5-nitro 2-cyano thiophene with 1:2 ratio.

Step B: Preparation of mixture of 5-cyano-2-(2-hydroxy-5-methoxybenzylidenimino)thiophene and 2-cyano-4-(2-hydroxy-5-methoxybenzylidenimino)thiophene A mixture of 1.0 g (6.5 mmole) of 2-cyano-5-nitro-thiophene and 2-cyano-4-nitro-thiophene was hydrogenated and reacted with 0.5 g of 2-hydroxy-5-methoxybenzaldehyde. The crude products were isolated as described in Example I and purified by column chromatography to give 0.26 g of 5-cyano-2-(2-hydroxy-5-methoxybenzylidenimino)thiophene and 0.14 g of 2- cyano-4-(2-hydroxy-5-methoxybenzylidenimino)thiophene.

Step C: Preparation of
5-cyano-2-(2-hydroxy-5-methoxybenzylamino)thiophene and
2-cyano-4-(2-hydroxy-5-methoxybenzylamino)thiophene Following substantially the same procedures as described in Example 3, 5-cyano-2-(2-hydroxy-5-methoxybenzylidenimino)thiophene was converted to 5-cyano-2-(2-hydroxy-5-methoxybenzylamino)thiophene, m.p. 86°–88° C. and 2-cyano-4-(2-hydroxy-5-methoxybenzylidenimino)thiophene was converted to 2-cyano-4-(2-hydroxy-5-methoxybenzylamino)thiophene, m.p. 114°–115° C.

EXAMPLE 8

5-Ethoxycarbonyl-2-(2-hydroxy-5-methoxybenzylamino)thiophene and
2-Ethoxycarbonyl-4-(2-hydroxy-5-methoxybenzylamino)thiophene Following substantially the same procedures as described in Example 6, the title compounds were prepared by nitration of 2-ethoxycarbonyl thiophene followed by reduction to the amine and reaction with 2-hydroxy-5-methoxybenzaldehyde followed by reduction with NaBH$_4$ to give 5-ethoxycarbonyl-2-(2-hydroxy-5-methoxybenzylamino)thiophen, m.p. 110.5°–112° C.; and 2-ethoxycarbonyl-4-(2-hydroxy-5-methoxybenzylamino)thiophene as an oil.

Similarly, the following pyrrole derivatives were prepared by nitration of 2-acetyl-1-methylpyrrole followed by reduction to the amines and reaction with 2-hydroxy-5-methoxybenzaldehyde followed by reduction with sodium borohydride to give 5-acetyl-2-(2-hydroxy-5-methoxybenzylamino)-1-methylpyrrole, m.p. 173°–175° C.; and 2-acetyl-4-(2-hydroxy-5-methoxybenzylamino)-1-methyl-pyrrole, m.p. 132°–133° C.

EXAMPLE 9

Set forth below are some illustrative topical formulations containing a selected active compound of the instant invention.

| Formulation Number 1 - Solution | |
|---|---|
| (a) 3-(3,5-dichloro-2-hydroxybenzylamino) [1,2,5] thiadiazole | 2.5% |
| Distilled water qs to | 100% |

Procedure: Dissolve compound (a) in enough water to make 100%. Filter the solution. Apply to the affected area.

| Formulation Number 2 - Tincture | |
|---|---|
| (b) 2-(2-hydroxy-5-methoxybenzyl-amino)-thiophene | 2.5% |
| Alcohol U.S.P. | 50% |
| Water qs to | 100% |

Procedure: Dissolve compound (b) in the alcohol. Add sufficient water to make 100%. Filter and apply to affected area.

| Formulation Number 3 - Topical Aerosol | |
|---|---|
| (c) 5-acetyl-2-(2-hydroxy-5-methoxybenzylamino) thiophene | 2.5% |
| Alcohol U.S.P. | 5% |
| Isopropylmyristate | 5% |

Conventional halogenated hydrocarbon propellant qs 100% e.g., Freon 11(trichlorofuluromethane), Freon 12(dichlorodifluoromethane), Freon 14 (carbon tetrafluoride), Freon C 318 (Octafluorocyclobutane), Freon 114(Cryofluorane), etc.

Procedure: Dissolve Compound (c) in the alcohol and isopropylmyristate. Add sufficient halogenated propellant and introduce into conventional aerosol containers either by pressure or by cold filing. Apply to affected area.

| Formulation Number 4 - Ointment | |
|---|---|
| 4-(2-hydroxy-5-methoxybenzylamino)-2,1,3-benzothiadiazole | 2.5% |
| Petrolatum U.S.P. qs to | 100% |

Procedure: Heat the petrolatum to 60° C. Add compound (d) and stir until thoroughly dispersed. Cool to room temperature. Apply to affected area.

What is claimed is:

1. A compound of formula (I)

$$(R)_n \underset{}{\underset{}{\bigcirc}} \begin{array}{c} OH \\ NHR^1 \end{array} \quad (I)$$

or a pharmaceutically acceptable salt thereof wherein R is
 (a) hydrogen;
 (b) halo;
 (c) C$_{1-6}$alkoxy;
 (d) C$_{1-6}$alkylthio or C$_{1-6}$haloalkylthio;
 (e) C$_{1-6}$alkyl sulfinyl;
 (f) C$_{1-6}$alkyl sulfonyl;
 (g) phenyl C$_{1-6}$alkoxy;
 (h) C$_{1-6}$alkyl;
 (i) C$_{1-6}$alkenyl;
 (j) C$_{1-6}$alkanoyl;
 (k) —OCH$_2$O—;
 (l) —COOH;
 (m) phenyl;
 (n) phenoxy;
 (o) cyano;
 (p) hydroxy C$_{1-6}$alkyl; or
 (q) C$_{1-6}$alkanoyloxy;
R$^1$ is heteroaryl selected from a group consisting of
 (1) thienyl
 (2) benzothienyl
 (3) pyrryl;
 (4) thiadiazolyl;
 (5) benzothiadiazolyl;
 (6) benzimidazolyl;
the heteroaryl groups above can be unsubstituted or substituted with one or more of R$^3$ when R$^3$ represents H, CH$_3$, F, Cl, COCH$_3$, —CN —COOR$^4$ where R$^4$ represents C$_{1-6}$alkyl; n is 1 to 4.

2. The compound of claim 1, which is (a) 3-(3,5-dichloro-2-hydroxybenzylamino)[1,2,5]-thiadiazole;
(b) 2-(2-hydroxy-5-methoxybenzylamino)benzimidazole;
(c) 5-acetyl-2-(2-hydroxy-5-methoxybenzylamino)-thiophene;
(d) 4-(2-hydroxy-5-methoxybenzylamino)-1,2,5-benzothiadiazole;
(e) 2-(2-hydroxy-5-methoxybenzylamino)thiophene;
(f) 5-cyano-2-(2-hydroxy-5-methoxybenzylamino)thiophene;
(g) 2-cyano-4-(2-hydroxy-5-methoxybenzylamino)-thiophene;
(h) 5-ethoxycarbonyl-2-(2-hydroxy-5-methoxybenzylamino)thiophene;
(i) 2-ethoxycarbonyl-4-(2-hydroxy-5-methoxybenzylamino)thiophene;
(j) 5-acetyl-2-(2-hydroxy-5-methoxybenzylamino)-1-methyl-pyrrole; or
(k) 2-acetyl-4-(2-hydroxy-5-methoxybenzylamino)-1-methylpyrrole.

3. A method of decreasing topical inflammation which comprises the administration to a mammalian species in need of such treatment an effective amount of a compound of formula I:

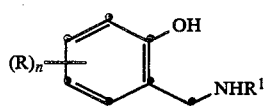

or a pharmaceutically acceptable salt thereof wherein:
R is
(a) hydrogen;
(b) halo;
(c) $C_{1-6}$alkoxy;
(d) $C_{1-6}$alkylthio or $C_{1-6}$haloalkylthio;
(e) $C_{1-6}$alkyl sulfinyl;
(f) $C_{1-6}$alkyl sulfonyl;
(g) phenyl $C_{1-6}$alkoxy;
(h) $C_{1-6}$alkyl;
(i) $C_{1-6}$alkenyl;
(j) $C_{1-6}$alkanoyl;
(k) —OCH$_2$O—;
(l) —COOH;
(m) phenyl;
(n) phenoxy;
(o) cyano;
(p) hydroxy $C_{1-6}$alkyl; or
(q) $C_{1-6}$alkanoyloxy;

$R^1$ is heteroaryl selected from a group consisting of
(1) thienyl;
(2) benzothienyl;
(3) furyl;
(4) benzofuryl;
(5) pyrryl;
(6) indolyl;
(7) thiazolyl;
(8) benzoythiazolyl;
(9) thiadiazolyl;
(10) benzothiadiazolyl;
(11) imidiazolyl;
(12) benzimidazolyl;
(13) quinolyl;
(14) isoquinolyl;
(15) pyridyl;
(16) pyrazinyl;
(17) tetrazolyl; or
(18) triazolyl the heteroaryl groups above can be unsubstituted or substituted with one or more of $R^3$ where $R^3$ represents H, CH$_3$, F, Cl, COCH$_3$, —CN or —COOR$^4$ where $R^4$ represents $C_{1-6}$alkyl;
n is 1 to 4.

4. The method of claim 3 wherein:
R is
(a) hydrogen;
(b) $C_{1-6}$alkoxy;
(c) $C_{1-6}$alkylthio or $C_{1-6}$alkylthio;
(d) halo;
(e) $C_{1-6}$alkanoyl;
(f) $C_{1-6}$haloalkyl;
(g) hydroxy $C_{1-6}$alkyl;
(h) cyano; or
(i) —OCH$_2$O—;

$R^1$ is

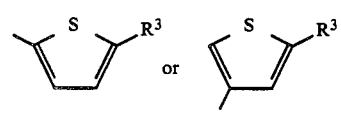 (1)

where $R^3$ represents H, CH$_3$, F, Cl, —COCH$_3$, —CN or —COOR$^4$ where $R^4$ represents loweralkyl;

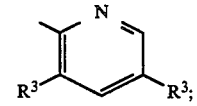 (2)

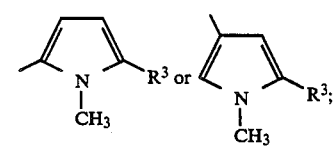 (3)

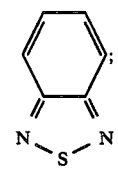 (4)

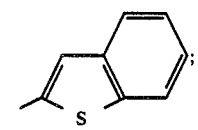 (5)

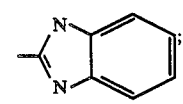 (6)

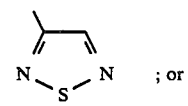 (7)

; or

-continued

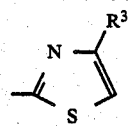

and n is 1 to 4.

5. The method of claim 3 wherein R is
(a) hydrogen;
(b) $C_{1-3}$alkoxy;
(c) $C_{1-3}$haloalkylthio;
(d) $C_{1-3}$alkanoyl; or
(e) fluoro or chloro;

$R^1$ is

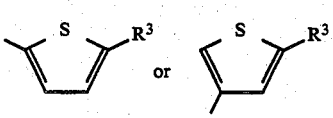

(1)

where $R^3$ represents H, CH$_3$, F, Cl, —COCH$_3$, —CN or —COOR$^4$ where $R^4$ represents loweralkyl;

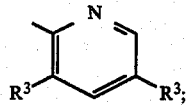

(2)

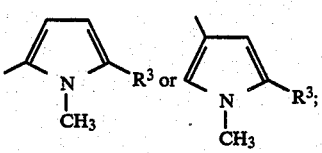

(3)

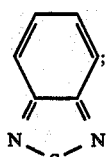

(4)

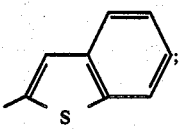

(5)

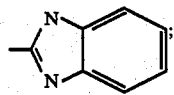

(6)

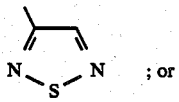

(7)

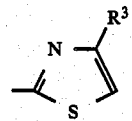

(8)

and n is 1 or 2.

6. The method of claim 3 wherein the compound is (a) 3-(3,5-dichloro-2-hydroxybenzylamino)[1,2,5]-thiadiazole;
(b) 2-(2-hydroxy-5-methoxybenzylamino)benzimidazole;
(c) 5-acetyl-2-(2-hydroxy-5-methoxybenzylamino)-thiophene;
(d) 4-(2-hydroxy-5-methoxybenzylamino)-1,2,5-benzothiadiazole;
(e) 2-(2-hydroxy-5-methoxybenzylamino)thiophene;
(f) 5-cyano-2-(2-hydroxy-5-methoxybenzylamino)thiophene;
(g) 2-cyano-4-(2-hydroxy-5-methoxybenzylamino)-thiophene;
(h) 5-ethoxycarbonyl-2-(2-hydroxy-5-methoxybenzylamino)thiophene;
(i) 2-ethoxycarbonyl-4-(2-hydroxy-5-methoxybenzylamino)thiophene;
(j) 5-acetyl-B 2-(2-hydroxy-5-methoxybenzylamino)-1-methyl-pyrrole; or
(k) 2-acetyl-4-(2-hydroxy-5-methoxybenzylamino)-1-methylpyrrole.

7. A pharmaceutical composition for treating topical inflammation comprising a pharmaceutical carrier and a therapeutically effective amount of a compound of formula I

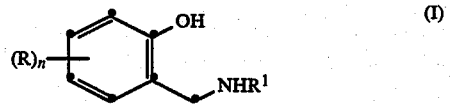

(I)

or a pharmaceutically acceptable salt thereof wherein:
R is
(a) hydrogen;
(b) halo;
(c) $C_{1-6}$alkoxy;
(d) $C_{1-6}$alkylthio or $C_{1-6}$haloalkylthio;
(e) $C_{1-6}$alkyl sulfinyl;
(f) $C_{1-6}$alkyl sulfonyl;
(g) phenyl $C_{1-6}$alkoxy;
(h) $C_{1-6}$alkyl;
(i) $C_{1-6}$alkenyl;
(j) $C_{1-6}$alkanoyl;
(k) —OCH$_2$O—;
(l) —COOH;
(m) phenyl;
(n) phenoxy;
(o) cyano;
(p) hydroxy $C_{1-6}$alkyl; or
(q) $C_{1-6}$alkanoyloxy;

$R^1$ is heteroaryl selected from a group consisting of
(1) thienyl;
(2) benzothienyl;
(3) furyl;
(4) benzofuryl;
(5) pyrryl;
(6) indolyl;
(7) thiazolyl;
(8) benzoythiazolyl;
(9) thiadiazolyl;
(10) benzothiadiazolyl;
(11) imidiazolyl;
(12) benzimidazolyl;
(13) quinolyl;
(14) isoquinolyl;
(15) pyridyl;
(16) pyrazinyl;

(17) tetrazolyl; or
(18) triazolyl the heteroaryl groups above can be unsubstituted or substituted with one or more of $R^3$ where $R^3$ represents H, $CH_3$, F, Cl, $COCH_3$, —CN or —$COOR^4$ where $R^4$ represents $C_{1-6}$alkyl;
n is 1 to 4.

8. The composition of claim 7 wherein R is
   (a) hydrogen;
   (b) $C_{1-6}$alkoxy;
   (c) $C_{1-6}$alkylthio or $C_{1-6}$alkylthio;
   (d) halo;
   (e) $C_{1-6}$alkanoyl;
   (f) $C_{1-6}$haloalkyl;
   (g) hydroxy $C_{1-6}$alkyl;
   (h) cyano; or
   (i) —$OCH_2O$—;

$R^1$ is

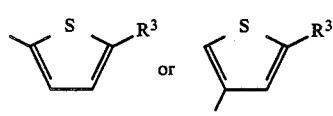
(1)

where $R^3$ represents H, $CH_3$, F, Cl, —$COCH_3$, —CN or —$COOR^4$ where $R^4$ represents loweralkyl;

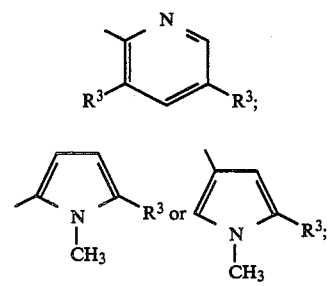
(2)

(3)

(4)

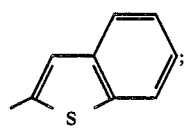
(5)

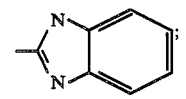
(6)

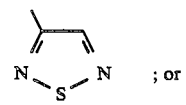
(7)

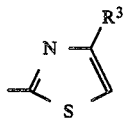
; or (8)

and n is 1 to 4.

9. The composition of claim 8 wherein R is
   (a) hydrogen;
   (b) $C_{1-3}$alkoxy;
   (c) $C_{1-3}$haloalkylthio;
   (d) $C_{1-3}$alkanoyl; or
   (e) fluoro or chloro;

$R^1$ is

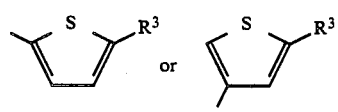
(1)

where $R^3$ represents H, $CH_3$, F, Cl, —$COCH_3$, —CN or —$COOR^4$ where $R^4$ represents loweralkyl;

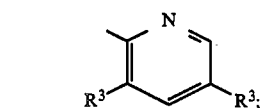
(2)

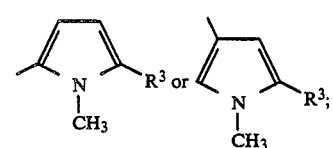
(3)

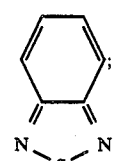
(4)

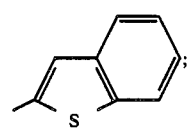
(5)

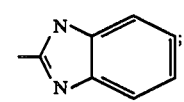
(6)

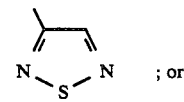
; or
(7)

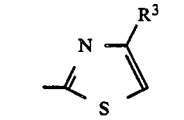
(8)

and n is 1 or 2.

10. The composition of claim 9 wherein the compound to be prepared is
    (a) 3-(3,5-dichloro-2-hydroxybenzylamino)[1,2,5]-thiadiazole;
    (b) 2-(2-hydroxy-5-methoxybenzylamino)benzimidazole;
    (c) 5-acetyl-2-(2-hydroxy-5-methoxybenzylamino)-thiophene;

(d) 4-(2-hydroxy-5-methoxybenzylamino)-1,2,5-benzothiadiazole;
(e) 2-(2-hydroxy-5-methoxybenzylamino)thiophene;
(f) 5-cyano-2-(2-hydroxy-5-methoxybenzylamino)thiophene;
(g) 2-cyano-4-(2-hydroxy-5-methoxybenzylamino)thiophene;
(h) 5-ethoxycarbonyl-2-(2-hydroxy-5-methoxybenzylamino)thiophene;
(i) 2-ethoxycarbonyl-4-(2-hydroxy-5-methoxybenzylamino)thiophene;
(j) 5-acetyl-2-(2-hydroxy-5-methoxybenzylamino)-1-methyl-pyrrole; or
(k) 2-acetyl-4-(2-hydroxy-5-methoxybenzylamino)-1-methylpyrrole.

* * * * *